US012560542B2

(12) United States Patent　　　　(10) Patent No.: US 12,560,542 B2

Wachernig et al.　　　　　　　　　　(45) Date of Patent: Feb. 24, 2026

(54) DEVICE AND METHOD FOR REDUCING THE FADING OF A FLUORESCENCE DYE BY LASER LIGHT WHEN DETERMINING FLUORESCENCE AND THE NUMBER OF ANTIBODIES ON EXOSOMES

(71) Applicant: PARTICLE METRIX GMBH, Inning am Ammersee (DE)

(72) Inventors: Hanno Wachernig, Diessen a. A. (DE); Clemens Helmbrecht, Seefeld (DE); Jens Schiffmann, Woerthsee (DE)

(73) Assignee: PARTICLE METRIX GMBH, Inning am Ammersee (DE)

( * ) Notice: Subject to any disclaimer, the term of this patent is extended or adjusted under 35 U.S.C. 154(b) by 1007 days.

(21) Appl. No.: 17/617,231

(22) PCT Filed: Jul. 6, 2020

(86) PCT No.: PCT/DE2020/000149
§ 371 (c)(1),
(2) Date: Dec. 7, 2021

(87) PCT Pub. No.: WO2021/004563
PCT Pub. Date: Jan. 14, 2021

(65) Prior Publication Data
US 2022/0236188 A1　　Jul. 28, 2022

(30) Foreign Application Priority Data
Jul. 11, 2019　(DE) ..................... 10 2019 004 870.9

(51) Int. Cl.
G01N 21/64　(2006.01)
G01N 33/58　(2006.01)

(52) U.S. Cl.
CPC ..... G01N 21/6456 (2013.01); G01N 21/6428 (2013.01); G01N 33/582 (2013.01);
(Continued)

(58) Field of Classification Search
CPC ........... G01N 21/6456; G01N 21/6428; G01N 21/6458; G01N 21/645; G01N 21/6452;
(Continued)

(56) References Cited

U.S. PATENT DOCUMENTS

| 4,777,133 A | 10/1988 | Picciolo |
| 2002/0030811 A1 | 3/2002 | Schindler |

(Continued)

FOREIGN PATENT DOCUMENTS

| CN | 101793678 | 8/2010 |
| CN | 107202762 | 9/2017 |

(Continued)

OTHER PUBLICATIONS

Espacenet English Translation of DE202018005287U1. (Year: 2019).*
(Continued)

*Primary Examiner* — Kathryn Elizabeth Limbaugh
(74) *Attorney, Agent, or Firm* — DUANE MORRIS LLP; Gregory M. Lefkowitz; Brandon A. Chan

(57)　　　　ABSTRACT

The invention relates to a device and method for reducing the reduction in intensity of a fluorescence dye by laser light when determining fluorescence and the number of antibodies on exosomes, comprising means for storing different measurement points of various differently coloured lasers in a measuring cell at certain measurement positions, the focusing of the laser beam interacting with the sample being recorded in a video camera as the centre of a convergent beam bundle.

3 Claims, 4 Drawing Sheets

Figure 1:
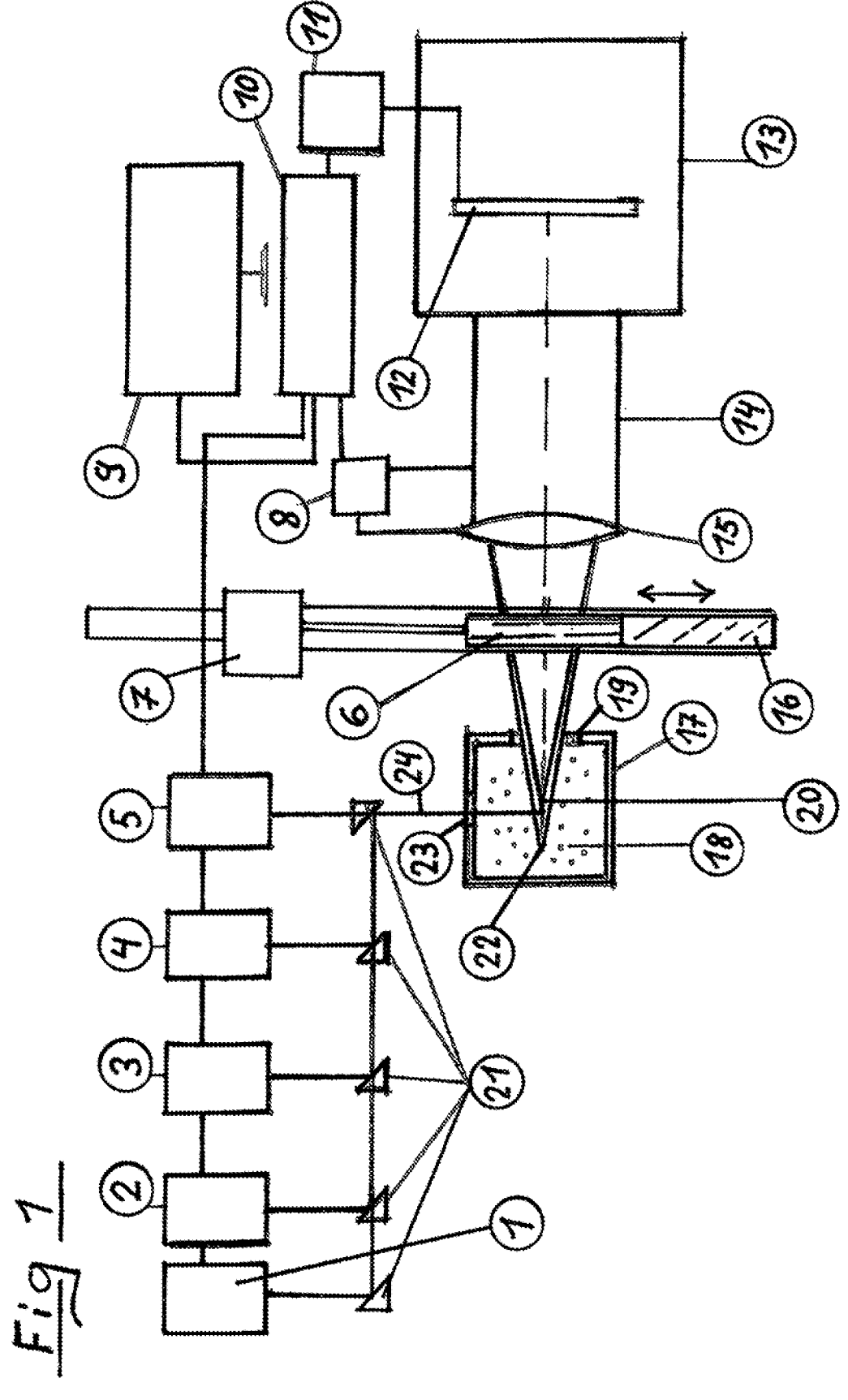

(52) U.S. Cl.
CPC ................ *G01N 2021/6419* (2013.01); *G01N 2021/6439* (2013.01); *G01N 2021/6471* (2013.01); *G01N 2201/127* (2013.01)

(58) Field of Classification Search
CPC ............... G01N 33/582; G01N 33/542; G01N 33/54313; G01N 2021/6419; G01N 2021/6439; G01N 2021/6471; G01N 2021/6421; G01N 2201/127; G01N 2201/1222; G01N 15/1434; G01N 15/0211; G01N 15/1425; G01N 15/1456; G01N 15/1459; G01N 15/0053; G01N 15/0222; G01N 15/1006; G01N 15/1027; G01N 15/1029; G01N 15/1438; G01N 15/1447; G01N 2015/0038; G01N 27/44721; G01N 2474/20
See application file for complete search history.

(56) References Cited

U.S. PATENT DOCUMENTS

| | | | |
|---|---|---|---|
| 2006/0089554 | A1 | 4/2006 | Ishihara |
| 2007/0114362 | A1 | 5/2007 | Feng |
| 2009/0108214 | A1 | 4/2009 | Shinoda |
| 2013/0037729 | A1* | 2/2013 | Hell .................. G01N 21/6428 |
| | | | 250/459.1 |
| 2013/0323745 | A1 | 12/2013 | Wainwright |
| 2019/0277743 | A1 | 9/2019 | Wachering |

FOREIGN PATENT DOCUMENTS

| | | |
|---|---|---|
| CN | 108956567 | 12/2018 |
| DE | 202018005287 | 1/2019 |
| DE | 202019002937 | 12/2019 |
| EP | 2594981 A2 | 5/2013 |
| JP | H0829324 | 2/1996 |
| JP | 20050091701 | 4/2005 |

OTHER PUBLICATIONS

C. Helmbrecht, et al., "High efficiency quantification of fluorescent labeled EVs with F-NTA", May 17, 2017, URL: https://www.particle-metrix.de/fileadmin/pdf_technologien/Poster_A0_Fluorescence_EN.pdf.

* cited by examiner

DEVICE AND METHOD FOR REDUCING THE FADING OF A FLUORESCENCE DYE BY LASER LIGHT WHEN DETERMINING FLUORESCENCE AND THE NUMBER OF ANTIBODIES ON EXOSOMES

CROSS-REFERENCE TO RELATED APPLICATIONS

This application is a § 371 national stage entry of International Application No. PCT/DE2020/000149, filed on Jul. 6, 2020, which claims priority to German Patent Application No. 10 2019 004 870.9, filed on Jul. 11, 2019, the entire contents of which are incorporated herein by reference.

The application relates to a device for reducing the intensity reduction of the fluorescence dye by laser light when determining the fluorescence and the number of antibodies on exosomes.

A device for determining the fluorescence and the number of antibodies on exosomes is known from DE 20 2018 005 287 U1.

Vesicles in biology are intracellular, very small, round to oval bubbles, which are enclosed by a single or double membrane or a reticulated envelope made of proteins. The vesicles form separate cell compartments in which different cellular processes run. Their size is approximately one micrometer. Vesicles are responsible for the transport of many materials in the cell.

The mechanisms which result in the occurrence of extracellular vesicles have not been completely explained up to this point. Three types of extracellular vesicles are differentiated on the basis of their origin or size.

In this case, exosomes are small vesicles having a size of approximately 50 to 150 nm.

According to claim 1 of this document, it relates to a device having the following features:

a) the beams of multiple different lasers (1, 2, 3, 4) are each directed by means of a separate collecting prism (14) separately on a beam path (21) in a measurement cell (22) having a sample (9) containing particles, wherein the focusing of the laser beam (21), in interaction with the sample (9), forms the center of a convergent beam bundle, consisting of light from the fluorescence plane (5) and the scattered light plane (8), which, after passing through a liquid lens having an optical unit controller (18), is registered in a video camera (15), b) the convergent beam path passes through a color filter (16), which is moved by means of a change wheel (17) and a controller (26), c) a display (19) having a touchscreen (19) and an overall controller (20) having a particle tracking program are used to operate a video camera (15).

Multiple measurements in succession using the same sample to achieve a statistically good result cannot be carried out in the case of the described prior art in DE 20 2018 005 287 U1, since the fluorescence dye used here fades too strongly due to the long laser action time and requires a replacement of the sample in the measurement cell after measurement.

If the action time of the laser on the laser dye (fluorochrome) were shortened, the fading could be reduced and multiple measurements using the same sample could be enabled.

The present application is therefore based on the object of shortening the action time of the laser light on the fluorochrome (fluorescence dye).

The object was achieved by the device as follows:

A device for reducing the quality reduction of the fluorescence dye by means of laser light when determining the fluorescence and the number of antibodies on exosomes having the following features:

a) means for storing various measurement points 26 of various different-colored lasers in a measurement cell (17) at certain measurement positions, wherein the focusing of the respective laser beam (24) in interaction with the sample (18) is registered as a center of a convergent beam bundle in a video camera, b) a change device 7, for the notch filter 6 and a quartz glass 16 for setting and securing the same optical path lengths for the fluorescence light and the laser scattered light in the convergent beam path between the liquid lens (15) and the measurement locations 26 in the measurement cell (17), c) a display (9) having a touchscreen and an overall controller (10) having a particle tracking program are used to operate a video camera (13), and the video camera (13) has a graphene-based light sensor (12) having an associated controller (11) for the light sensor (12) and has rapid stepping motors and precision movement carriages free of play and the camera is a CMOS or an eCCD.

and the method as follows:

A method for reducing the intensity reduction of the fluorescence dye by laser light when determining the fluorescence and the number of antibodies on exosomes having the following features:

a) the measurement cell (17) is filled with test liquid to detect the various positions of the laser used, its focusing, and storage, b) the calibration liquid is replaced with sample liquid having exosomes to be measured, and the cell (17) is checked for freedom from bubbles, all lasers are moved back to position 1, c) the lasers used are moved in succession to their stored focus points and switched on at the beginning of the analysis, the images are recorded by the light sensor (12), and the corresponding data are passed on to the pattern recognition, and a computer program having a program code for carrying out the method steps when the program is executed in a computer, and a machine-readable carrier having the program code of a computer program for carrying out the method when the program is executed in a computer.

The figures of the application have the following content.

FIG. 1: shows an illustration of a special NTA nanoparticle tracking method.

Figure 2:
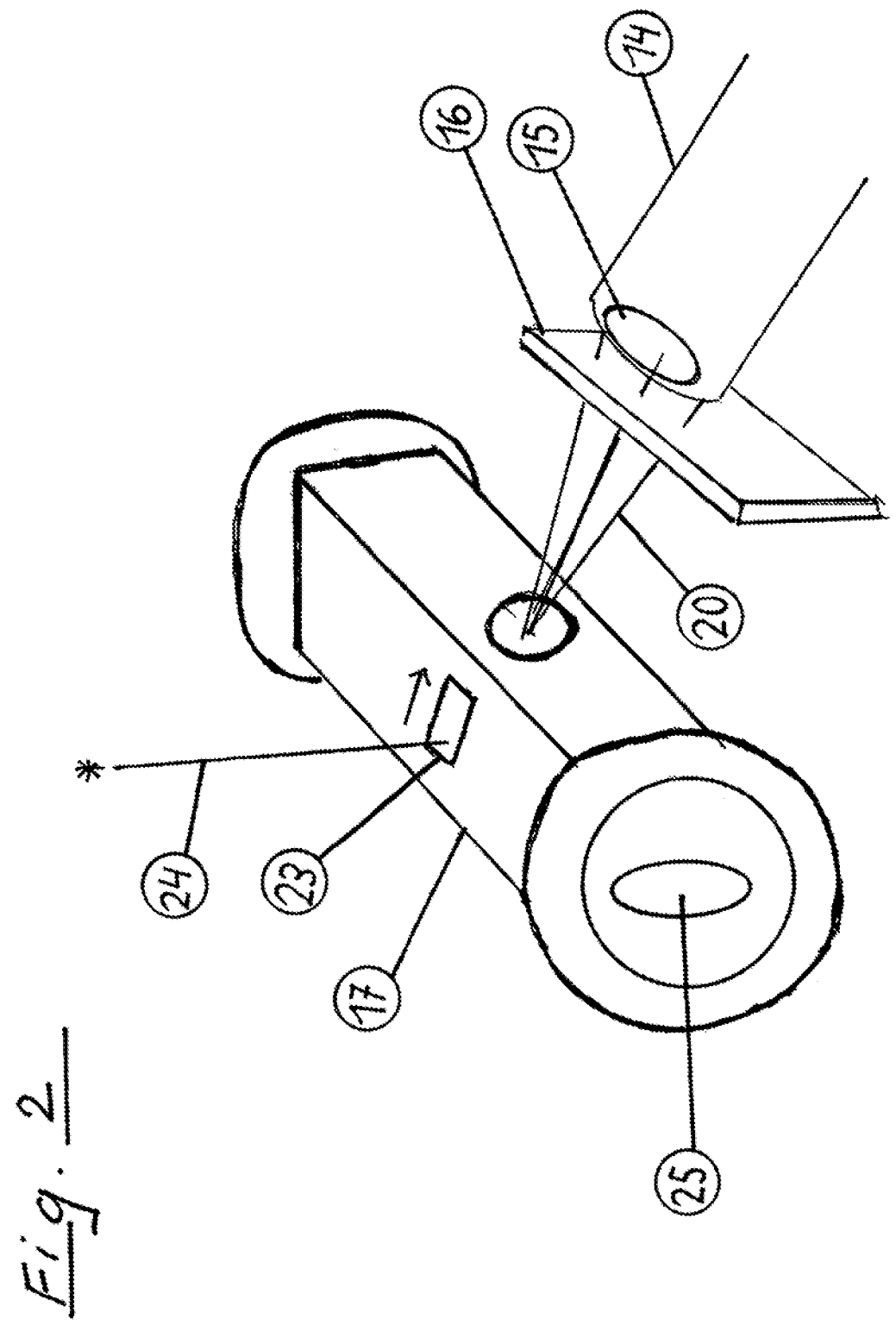

FIG. 2: shows an illustration of the measurement cell.

Figure 3:
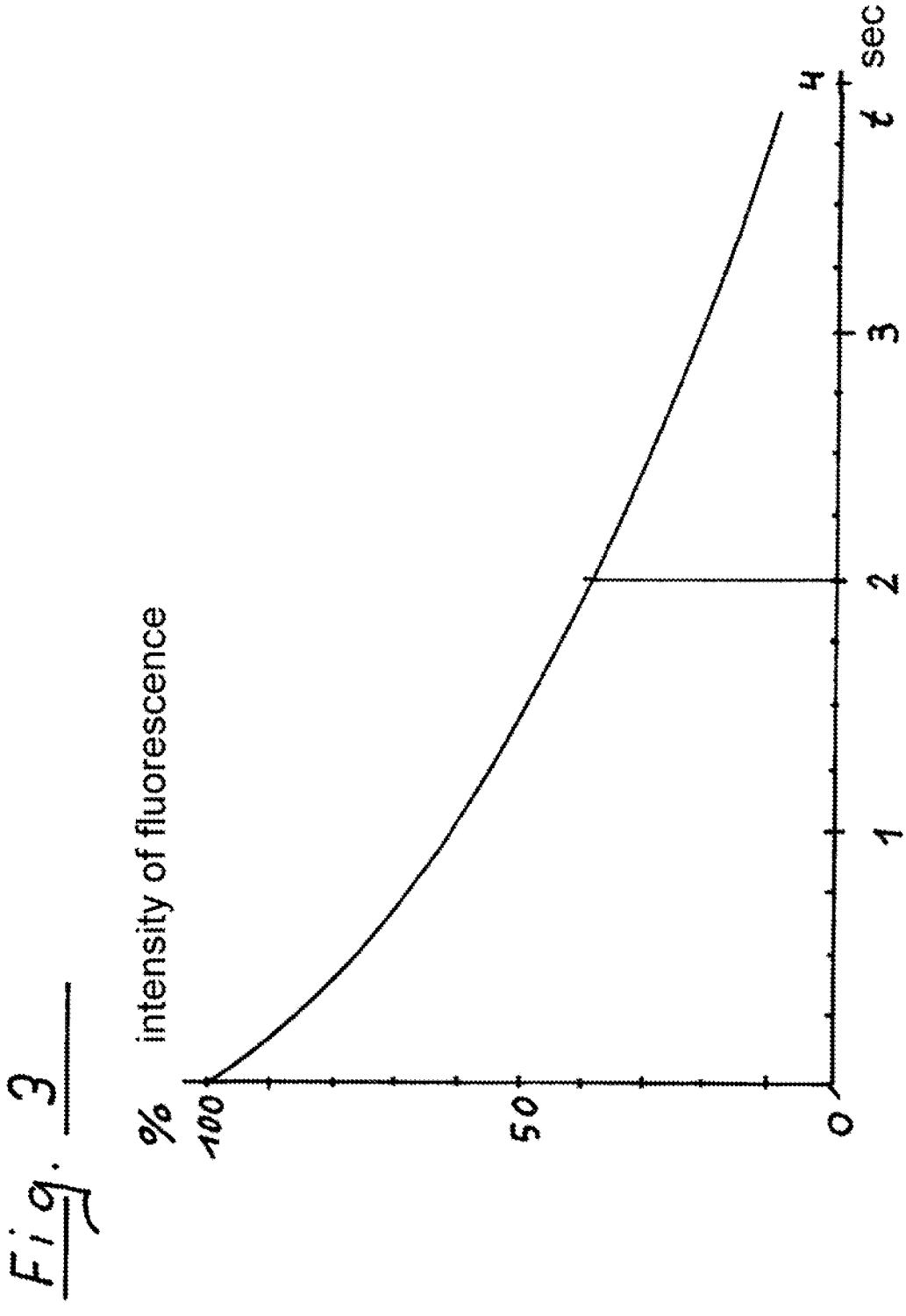

FIG. 3: shows an illustration of the reduction of the intensity of the dye after laser action in seconds.

Figure 4:
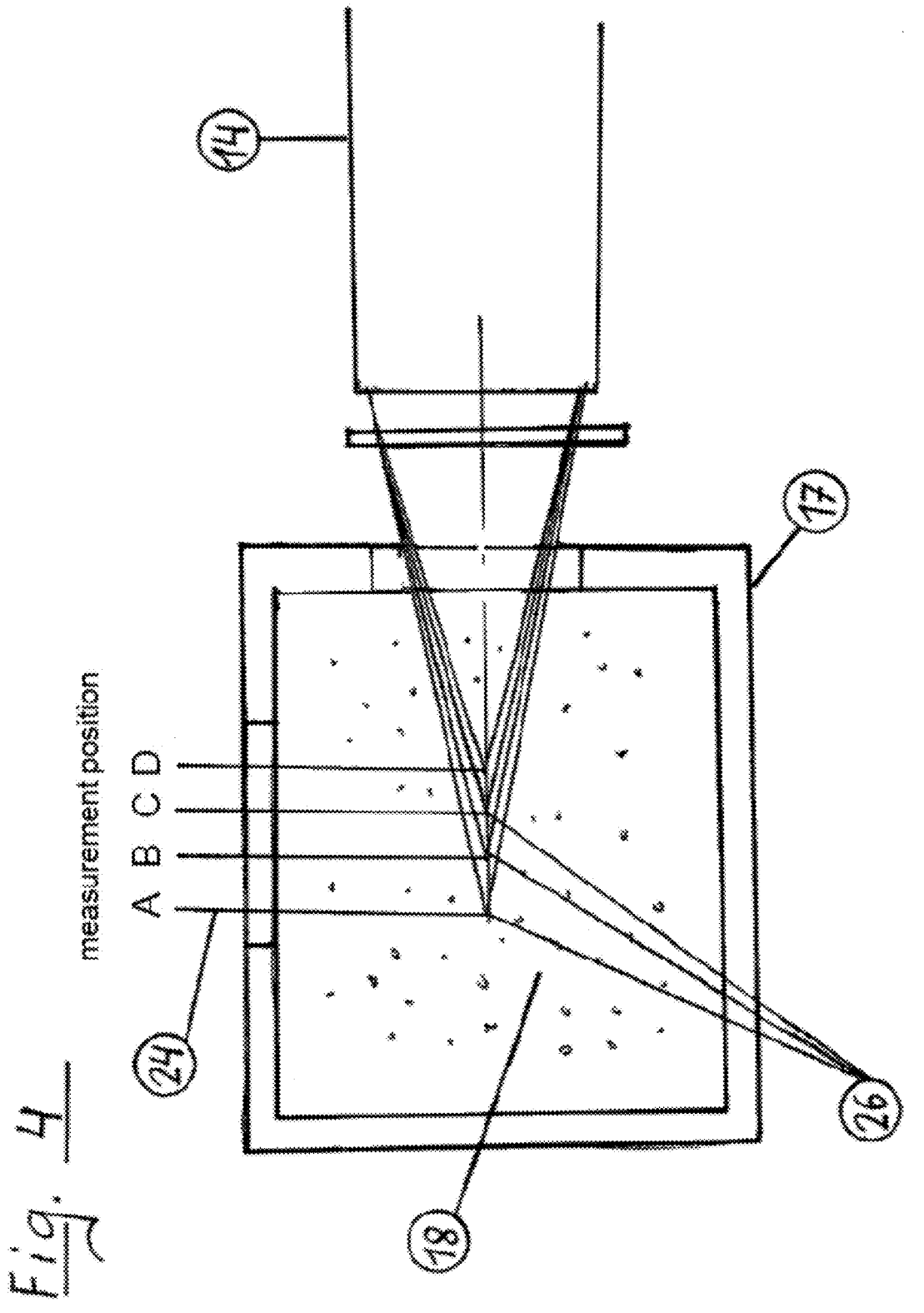

FIG. 4: shows an illustration of the measurement positions in the measurement cell and the focusing points of the laser (measurement points).

FIG. 1 corresponds in essential parts to the illustration of FIG. 1 from DE 20 2018 005 U1.

The number of the lasers is five instead of four in the prior art. The liquid filter 6 in the prior art is replaced by a notch filter 6 having an associated change device 7, for the notch filter 6 and a quartz glass 16. The quartz glass 16 is used to set and secure the same optical path lengths for the fluorescence light and the laser scattered light in the convergent beam path through the objective to the light sensor 12 during the adjustment of the measurement points 26 (see FIG. 4) in the measurement cell 17. The quartz glass simulates the same optical path lengths as the notch filter.

The video camera 15 in the prior art has the number 13 here and has a graphene-based light sensor 12 having a controller 11 for the light sensor 12 and controls, by means of the camera optical unit 14 via an optical unit controller 8, a liquid lens 15 which in turn via the notch filter 6 is incident in the fluorescence plane 20 in the sample 18 of the measurement cell 17 and the optical passage window 19 in the measurement cell 17 on a beam path 24 of one of the lasers 1 to 5 and one of the collecting prisms 21.

The overall controller 10 corresponds to the overall controller 20 in the prior art, wherein the display 9 corresponds to the corresponding display 19.

The illustration of the measurement cell 17 in FIG. 2 shows, vertically from the top, the beam path also shown in FIG. 1—laser 24 which passes through the laser passage window 23, wherein laterally the focus of the fluorescence plane 20 tapering to a point passes through the quartz glass 16, out of the liquid lens 15 and the camera optical unit 14.

The filling opening 25 of the measurement cell 17 can be seen on the front side.

The reduction of the intensity of the dye after the laser action in seconds can be seen well in percentage in FIG. 3. The laser light is to act at most 2 seconds on the fluorescence at the measurement location 26. The intensity of the fluorescence dye then becomes too weak and does not supply usable measurement results.

The illustration of the measurement positions in the measurement cell 17 and the measurement locations 26 for the focusing points (the laser scattered light plane and the fluorescence light plane) of the optical unit to the beam path of the laser 24 can be inferred from the various measurement positions A to D shown in FIG. 4. The camera optical unit 14 is also shown here.

For example, the 4 positions shown in FIG. 4 are carried out hereinafter using the arrangement according to FIG. 1.

The measurement cell 17 is filled using test liquid, wherein this test liquid contains polystyrene particles or certified exosome standards instead of the exosome sample.

The individual lasers are then guided in the respective measurement point 26 of the measurement cell 17 (see FIG. 4) and stored.

That is to say, all 5 lasers are each guided into the measurement position A, and the optical path lengths are ascertained, focused, and then stored. Furthermore, all 5 lasers are then guided into the next measurement position, focused, and then stored.

This is also carried out with the position C and the position D and all 5 lasers.

The lasers are then switched off.

As the next step, the calibration liquid is replaced with a sample liquid having exosomes in the measurement cell.

As the next step, the notch filter 6 is pushed between the liquid lens 15 and the measurement cell 17 and moved into the convergent beam path, wherein the quartz glass 16 is used for the fixing in conjunction with the device 7.

The actual measurement begins at measurement position A in that the five lasers are switched through in succession on their stored focus points and the images are recorded by the light sensor and the data are passed on to the pattern recognition. The time required for this purpose is less than two seconds. The lasers are then switched off.

The lasers move further to measurement position B. The measurement follows as in the preceding step. The lasers are then switched off.

The lasers move further to the measurement position C. The measurement again takes place as in the preceding step. The lasers are then switched off.

The lasers move to the measurement position D. The data are evaluated.

The particles can form high or low concentrations of particles of different levels at various points in the measurement cell. For example, due to the filling. Multiple measurement positions are thus necessary in the measurement cell to obtain a good quality and a high statistical certainty of the measurement.

In the newly approached measurement positions in the measurement cell, the fluorescence on the antibodies is still fresh and unused.

The fluorescence is further preserved by switching off the laser when moving to the next measurement position, since no laser light can cause fading. This is only possible due to the prior storage of the individual measurement positions and focus points and the high-precision rapid approach to the positions again. (Rapid stepping motors, precision movement carriages without play at the lasers and liquid lens in the objective).

The multi-band pass filter 6 (multi-notch filter) enables the rapid switching through of the individual lasers. A time saving thus results for preserving the fluorescence, since no filter change is necessary.

By way of the careful measurement method shown, not only four, as in our example, but up to 100 or more measurement positions having the measurement locations 26 can be approached and measured using five lasers in the same exosome fluorescence sample. This ensures a very high quality of the measurement.

In the camera, a high-sensitivity sCMOS or an eCCD or a graphene light sensor has to be used, since the multiband pass filter 6 (notch filter) reduces the light intensity.

The method requires a complex control of the described method and movement sequences by a special control and analysis program.

LIST OF REFERENCE NUMERALS

1 laser 375 nm
2 laser (violet=405 nm)
3 laser (blue=488 nm)
4 laser (green=520 nm)
5 laser (red=640 nm)
6 notch filter (multiband pass filter)
7 change device for the notch filter and the quartz glass
8 optical unit controller
9 display having touchscreen
10 overall controller having particle tracking program
11 controller for light sensor 12
12 graphene-based light sensor
13 detector or video camera eCCD, sCMOS
14 camera optical unit
15 liquid lens having settable focus
16 quartz glass
17 measurement cell
18 sample
19 optical unit passage window of the measurement cell 17
20 fluorescence plane
21 collecting prisms (guide all lasers into one beam path)
22 scattered light plane
23 laser passage window of the measurement cell 17
24 beam path laser
25 filling opening of the measurement cell 17

26 measurement location (measurement point having the focus planes for laser scattered light and fluorescence light)

We claim:

1. A device for reducing quality reduction of a fluorescence dye by means of laser light when determining a fluorescence and a number of antibodies on exosomes with the device, the device comprising:

a measurement cell (17) containing a sample liquid (18), different-colored lasers (1-5) and an associated collecting prism (21) for each of the lasers (1-5), wherein the device is configured to guide a beam from each of the lasers (1-5) via the associated collecting prism (21) to a single common incident beam (24) for all the lasers, a video camera (13) and a liquid lens (15) with an adjustable focus, means for storing device settings for a plurality of measurement points (26) of the lasers in the measurement cell (17) corresponding to a plurality of predetermined measurement positions (A-D) of the incident beam (24), wherein focusing of the respective incident beam (24) in interaction with the sample liquid (18) in the measurement cell (17) is registered as a center of a convergent beam bundle in the video camera (13), a change device (7), for a notch filter (6) and a quartz glass (16) for setting and securing same optical path lengths for fluorescence light and laser scattered light in a convergent beam path between the liquid lens (15) and the measurement points (26) in the measurement cell (17), a display (9) having a touchscreen and an overall controller (10) having a particle tracking program used to operate the video camera (13), and means for moving the lasers (1-5), so that the incident beam (24) is successively positioned at each of the plurality of predetermined measurement positions (A-D).

2. The device as claimed in claim 1, wherein the video camera (13) has a graphene-based light sensor (12) having an associated controller (11) for the graphene-based light sensor (12).

3. The device as claimed in claim 1, wherein the device has rapid stepping motors and precision movement carriages without play at the lasers (1-5) and the liquid lens (15) and the video camera is a sCMOS or an eCCD.

* * * * *